United States Patent
Tsai et al.

(10) Patent No.: US 8,002,995 B2
(45) Date of Patent: Aug. 23, 2011

(54) FLUID ANALYTICAL DEVICE

(75) Inventors: Chung-Hsien Tsai, Taipei County (TW); Cheng-Shiu Chung, Hsinchu (TW); Wen-Pin Hsieh, Miaoli County (TW)

(73) Assignee: Industrial Technology Research Institute, Hsinchu (TW)

( * ) Notice: Subject to any disclaimer, the term of this patent is extended or adjusted under 35 U.S.C. 154(b) by 126 days.

(21) Appl. No.: 12/060,682

(22) Filed: Apr. 1, 2008

(65) Prior Publication Data

US 2009/0114608 A1 May 7, 2009

(30) Foreign Application Priority Data

Nov. 2, 2007 (TW) ................................ 96141349 A

(51) Int. Cl.
*B01L 3/00* (2006.01)

(52) U.S. Cl. ...................... 210/787; 210/767; 210/512.1; 422/502; 422/506; 422/533; 422/548

(58) Field of Classification Search .................. 210/767, 210/787, 512.1, 360.1; 422/72, 63, 64, 67, 422/101, 502, 506, 533, 548; 436/45

See application file for complete search history.

(56) References Cited

U.S. PATENT DOCUMENTS

| | | | |
|---|---|---|---|
| 3,873,217 A * | 3/1975 | Anderson et al. | 356/246 |
| 4,154,793 A * | 5/1979 | Guigan | 422/55 |
| 5,061,381 A | 10/1991 | Burd | |
| 5,089,417 A | 2/1992 | Wogoman | |
| 5,472,603 A * | 12/1995 | Schembri | 210/380.1 |
| 5,916,522 A | 6/1999 | Boyd et al. | |
| 6,319,469 B1 * | 11/2001 | Mian et al. | 422/64 |
| 6,527,432 B2 * | 3/2003 | Kellogg et al. | 366/182.1 |
| 6,548,788 B2 | 4/2003 | Kellogg et al. | |
| 7,022,286 B2 * | 4/2006 | Lemke et al. | 422/67 |
| 7,026,131 B2 | 4/2006 | Hurt et al. | |
| 7,033,747 B2 | 4/2006 | Gordon | |
| 7,914,753 B2 * | 3/2011 | Tsai et al. | 422/506 |
| 2003/0166265 A1 * | 9/2003 | Pugia et al. | 435/288.3 |
| 2003/0219713 A1 * | 11/2003 | Valencia et al. | 435/4 |
| 2006/0133958 A1 | 6/2006 | Hsieh et al. | |
| 2006/0144802 A1 * | 7/2006 | Kitawaki et al. | 210/782 |
| 2011/0014094 A1 * | 1/2011 | Kim et al. | 422/400 |

FOREIGN PATENT DOCUMENTS

TW I243705 12/2004

OTHER PUBLICATIONS

Taiwan Patent Office, Office Action—Notice of Allowance, Patent Application Serial No. 096141349, Apr. 13, 2011, Taiwan.

* cited by examiner

*Primary Examiner* — Tony G Soohoo
*Assistant Examiner* — David C Mellon

(57) ABSTRACT

A fluid analytical device is provided including a body, a reservoir, an inlet channel and a separation unit. The reservoir is formed on the body. The inlet channel is formed on the body connected to the reservoir. The separation unit is formed on the body connected to the inlet channel, which includes a pile area, a collecting area and a spacer. The collecting area is located between the pile area and the reservoir. The spacer is formed between the pile area and the collecting area.

11 Claims, 13 Drawing Sheets

FLUID ANALYTICAL DEVICE

BACKGROUND OF THE INVENTION

1. Field of the Invention

The invention relates to a fluid analytical device, and more particularly to a fluid analytical device for separating constituents of blood.

2. Description of the Related Art

Conventional fluid analytical devices have complex structures. For example, U.S. Pat. No. 6,548,788 disclose a fluid analytical device with a micro-valve disposed on a body to stop flow. However, a micro-valve is manufactured by a micro manufacturing process, and cannot be formed by injection molding, thus, increasing costs.

U.S. Pat. No. 6,548,788 and U.S. Pat. No. 5,089,417 disclose other fluid analytical devices, which also have complex structures and high costs.

BRIEF SUMMARY OF THE INVENTION

A detailed description is given in the following embodiments with reference to the accompanying drawings.

A fluid analytical device comprises a body, a reservoir, an inlet channel and a separation unit. The reservoir is formed on the body. The inlet channel is formed on the body connected to the reservoir. The separation unit is formed on the body connected to the inlet channel, which comprises a pile area, a collecting area and a spacer. The collecting area is located between the pile area and the reservoir. The spacer is formed between the pile area and the collecting area.

The fluid analytical device of the invention quickly separates fluid with a simpler structure and lower cost.

BRIEF DESCRIPTION OF THE DRAWINGS

The invention can be more fully understood by reading the subsequent detailed description and examples with references made to the accompanying drawings, wherein:

FIG. 1b is an enlarged view of portion A of FIG. 1a;

FIG. 3b is an enlarge view of portion C of FIG. 3a;

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1A:
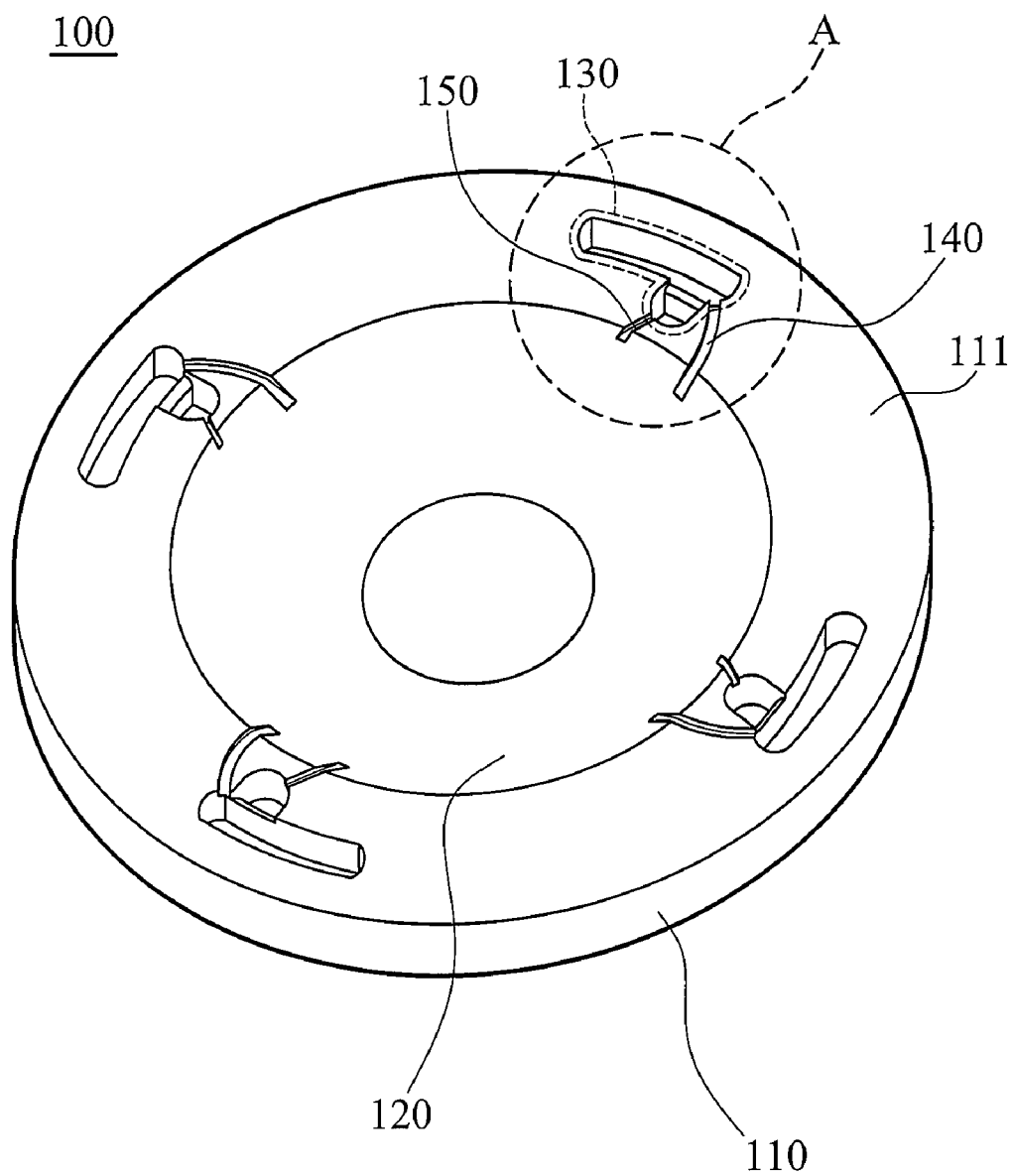
FIG. 1a shows a fluid analytical device of a first embodiment of the invention.

FIG. 1a shows a fluid analytical device 100 of a first embodiment of the invention, comprising a body 110, a reservoir 120, separation units 130, inlet channels 140 and exhaust channels 150. The body 110 is circular, comprising a first surface 111. The reservoir 120 is circular formed in a center of the body 110. The separation units 130 are near an edge of the body 110, and surround the reservoir 120 equidistantly. The inlet channels 140 are formed on the body 110 connecting the reservoir 120 and the separation unit 130. The exhaust channels 150 are formed on the body 110 connecting the reservoir 120 and the separation units 130.

Figure 1B:
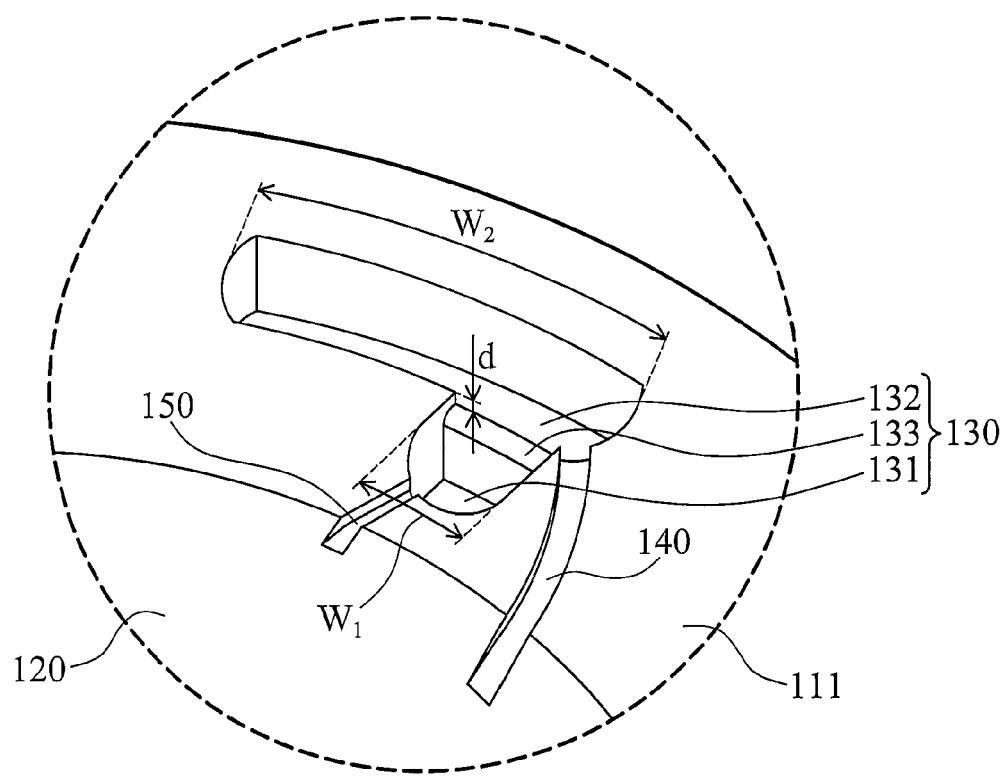

FIG. 1b is an enlarged view of portion A of FIG. 1a. Each separation 130 comprises a collecting area 131, a pile area 132 and a spacer 133. The collecting area 131 is located between the pile area 132 and the reservoir 120. The spacer 133 is located between the collecting area 131 and the pile area 132. The volume of the collecting area 131 is smaller than the volume of the pile area 132. A volume ratio between the pile area 132 and the collecting area 131 is between 1:1 and 2:1. A ratio between a depth d of the spacer 133 and a depth of the collecting area is about between ⅓ and ⅙. The width $W_2$ of the pile area 132 along a periphery direction is greater than the width $W_1$ of the collecting area 131 along the periphery direction. The inlet channel 140 connects the separation unit 130 in a location above the spacer 133. The exhaust channel 150 connects the collecting area 131 and the reservoir 120.

Figure 2A:
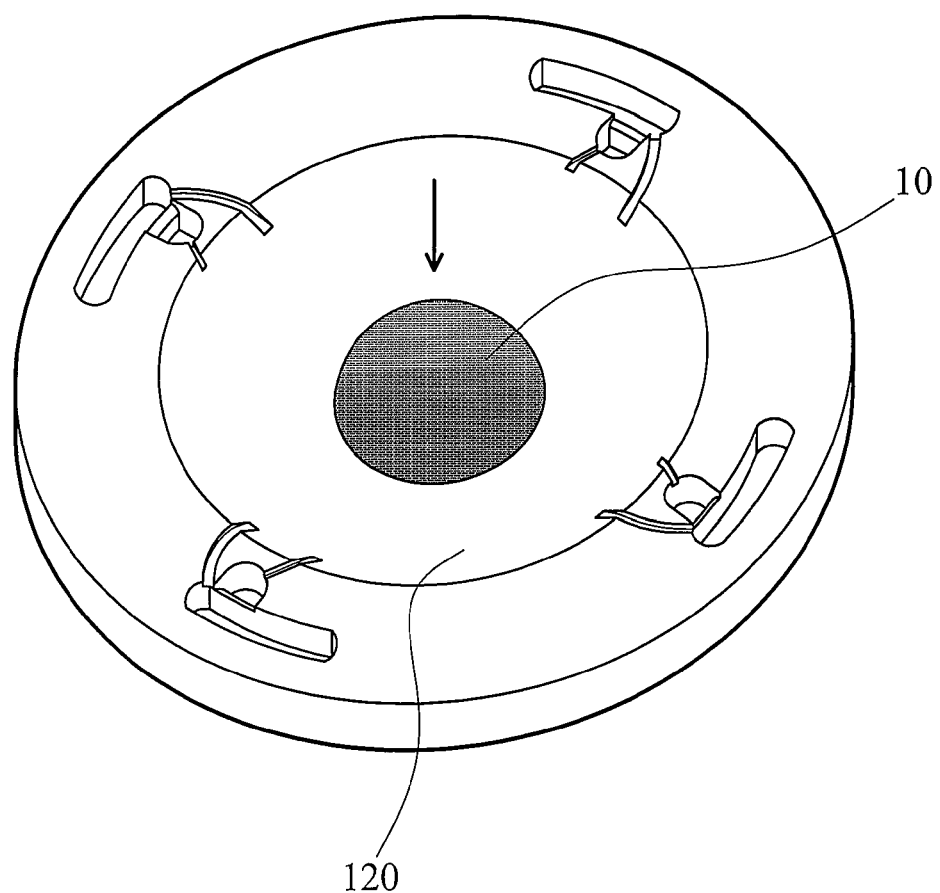
FIGS. 2a-2c show fluid separation process of the first embodiment of the invention.
Figure 2B:
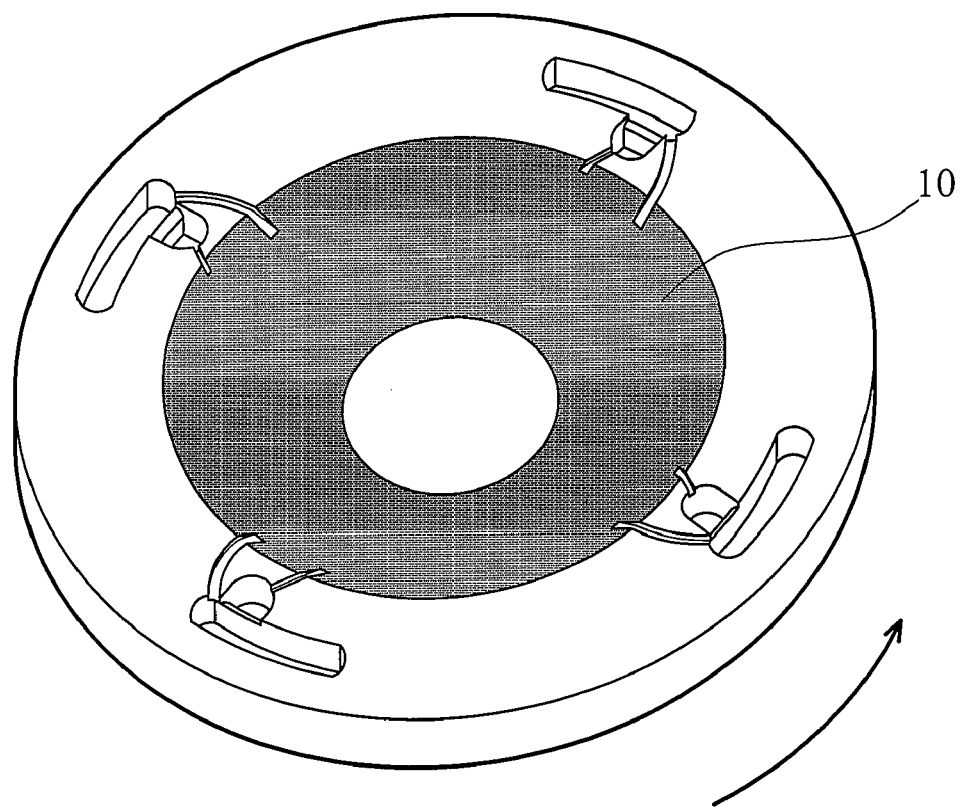
Figure 2C:
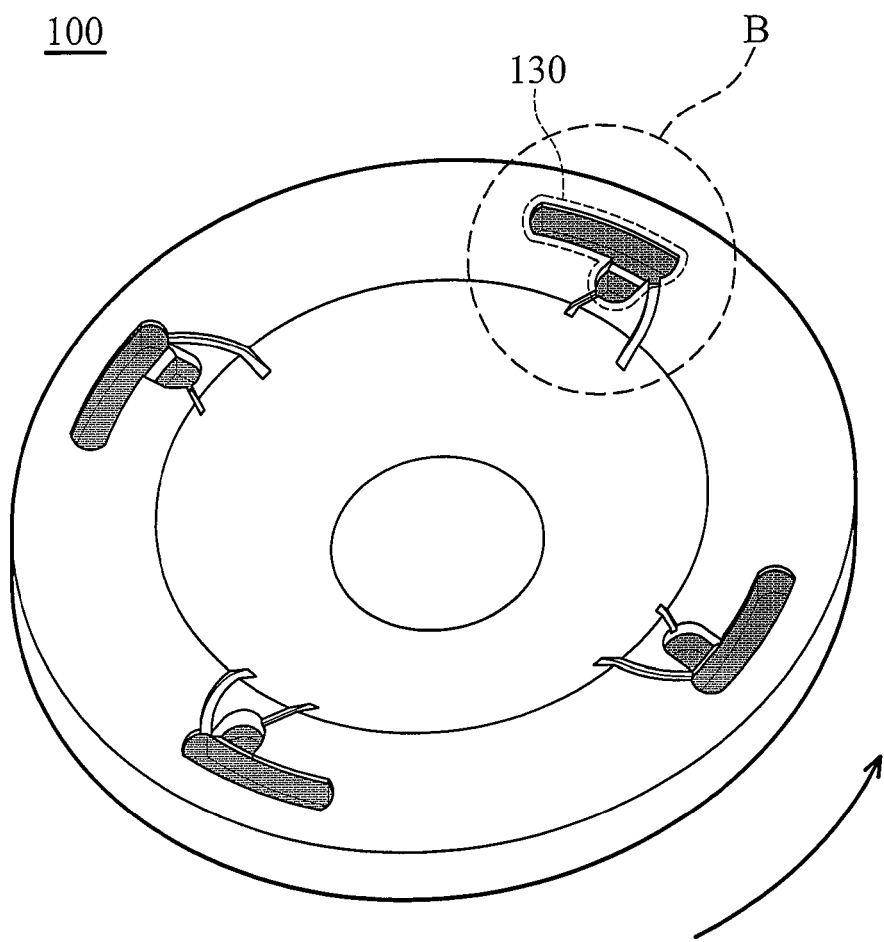
Figure 2D:
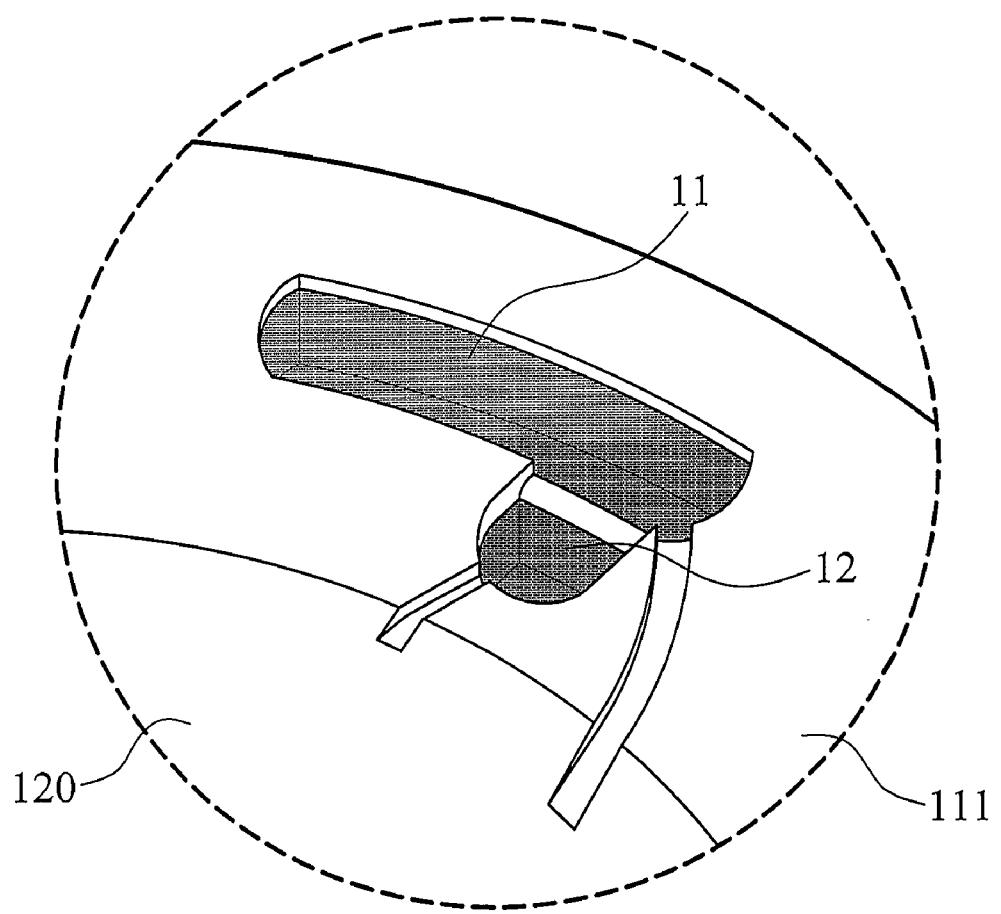
FIG. 2d is an enlarge view of portion B of FIG. 2c.

FIGS. 2a-2c show fluid separation process of the first embodiment of the invention. First, as shown in FIG. 2a, fluid (blood) 10 is infused in the center of the reservoir 120. Then, with reference to FIGS. 2b and 2c, the fluid analytical device 100 is rotated counterclockwise with respect to the reservoir 120 to move the fluid (blood) 10 into the separation units 130 by centrifugal force. FIG. 2d is an enlarge view of portion B of FIG. 2c, wherein the fluid (blood) 10 has been separated, a first fluid constituent (blood cells) 11 is gathered in the pile area 132, and a second fluid constituent (plasma) 12 is collected in the collecting area 131.

Figure 3A:
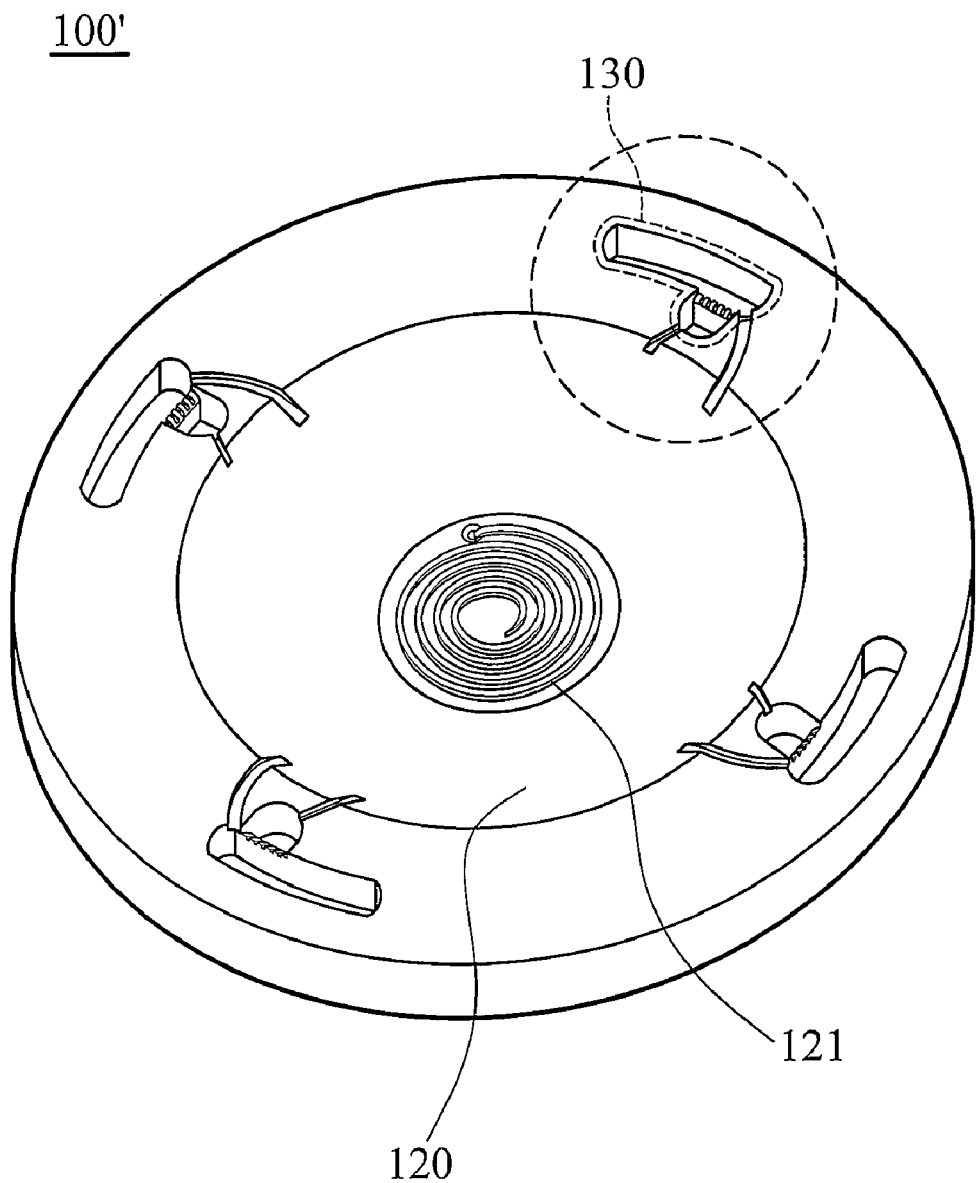
FIG. 3a shows a fluid analytical device of a modified example of the first embodiment.
Figure 3B:
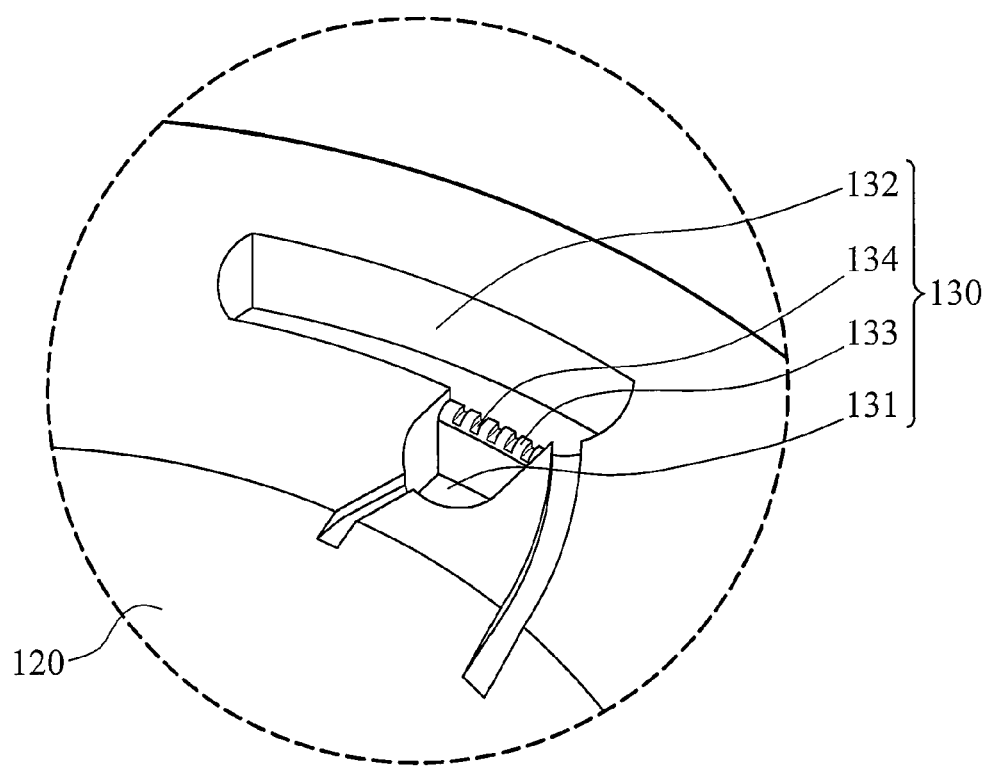

FIG. 3a shows a fluid analytical device 100' of a modified example of the first embodiment, wherein the reservoir 120 further comprises a spiral groove 121 formed on a bottom thereof for defining the quantity of the fluid 10. FIG. 3b is an enlarge view of portion C of FIG. 3a, wherein a plurality of guiding grooves 134 are formed on the top of the spacer 133. The guiding grooves 134 guide the first fluid constituent (blood cells) to the pile area 132 by capillarity.

Figure 4A:
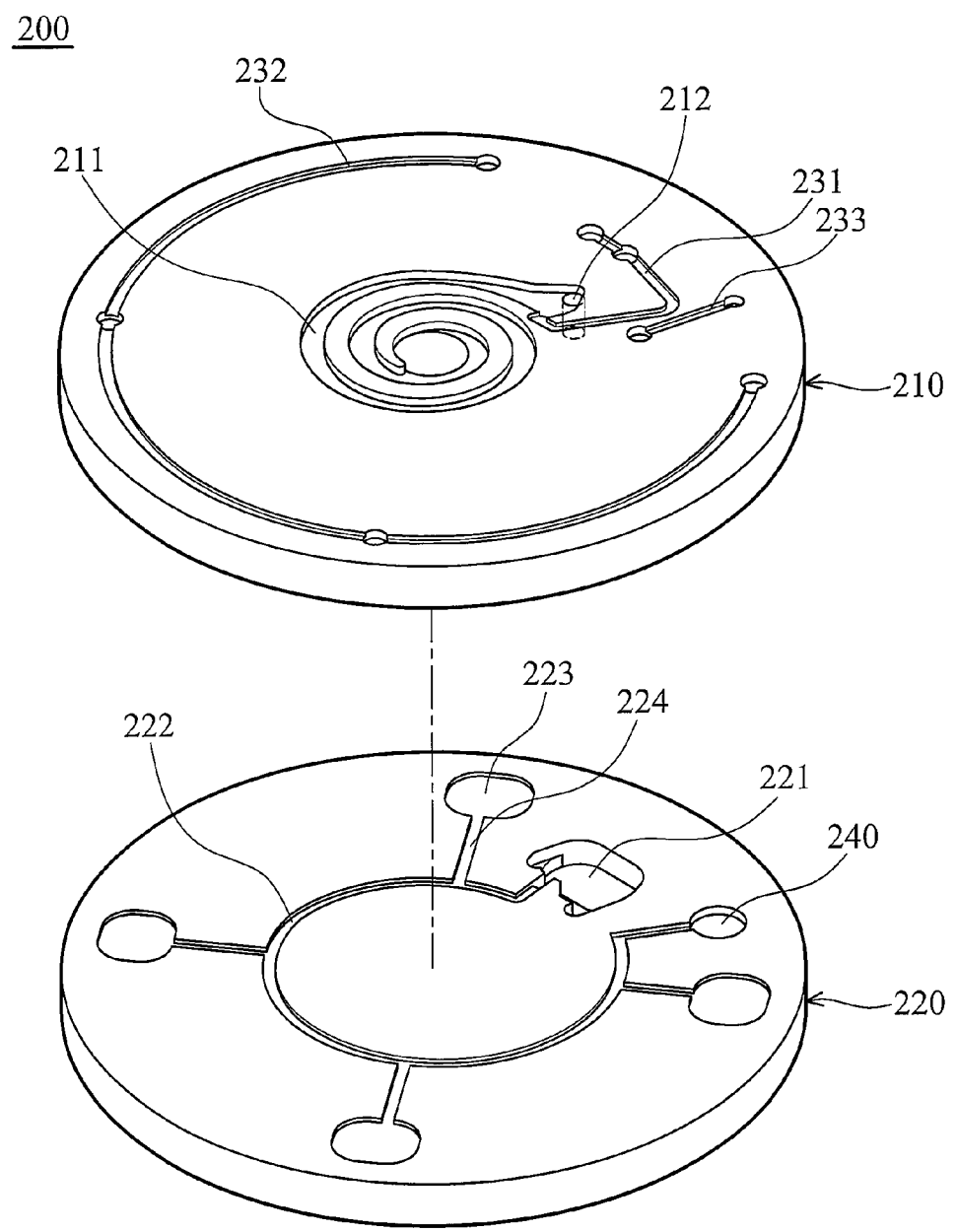
FIGS. 4a and 4b show a fluid analytical device of a second embodiment of the invention comprising a first body and a second body.
Figure 4B:
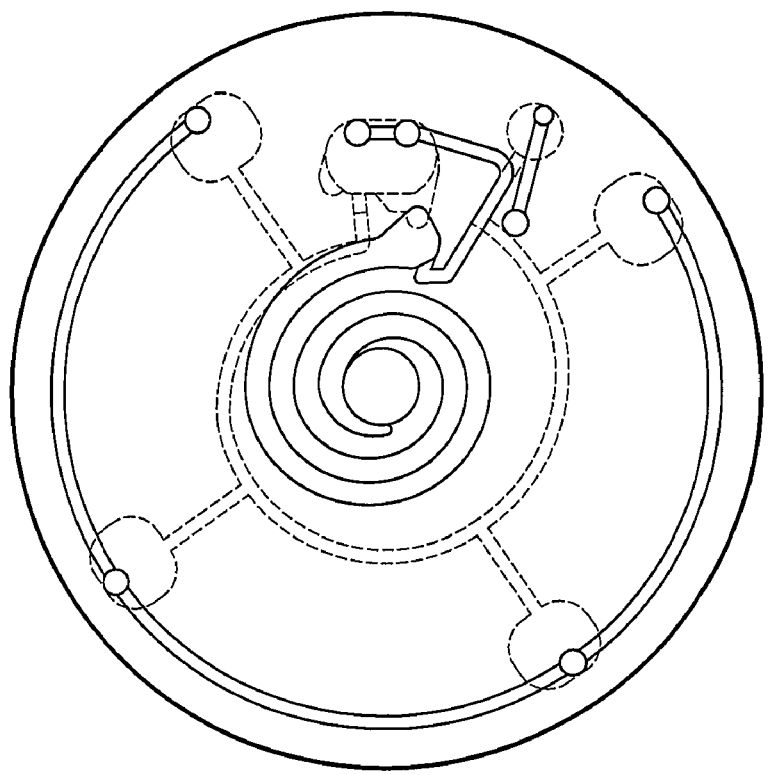

FIGS. 4a and 4b show a fluid analytical device 200 of a second embodiment of the invention comprising a first body 210 and a second body 220. The first body 210 comprises a spiral groove 211 and a first drain 212. The first drain 212 connects a bottom of the spiral groove 211 passing through the first body 210. The second body 220 comprises a first separation room 221, a second drain 222, collecting wells 223 and capillaries 224. The first separation room 221 connects the first drain 222. The second drain 222 connects to the first separation room 221. The second drain 222 is ring shaped. The capillaries 224 connect the collecting well 223 and the second drain 222.

The first body 210 further comprises a first exhaust drain 231, a second exhaust drain 232 and a third exhaust drain 233. The first exhaust drain 231 connects an upper portion of the spiral groove 211 and the first separation room 221. The second exhaust groove 232 is ring shaped and is connected to the collecting well 223.

The second body 220 further comprises a waste well 240. The waste liquid well 240 connects the second drain 222 and the third exhaust groove 233.

Figure 5A:
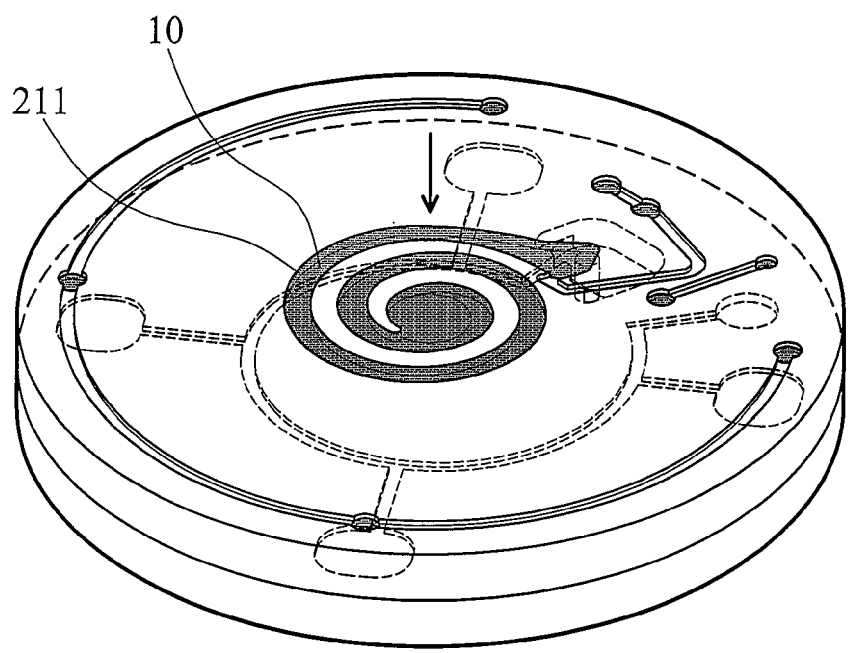
FIGS. 5a-5c show liquid separation process of the fluid analytical device.
Figure 5B:
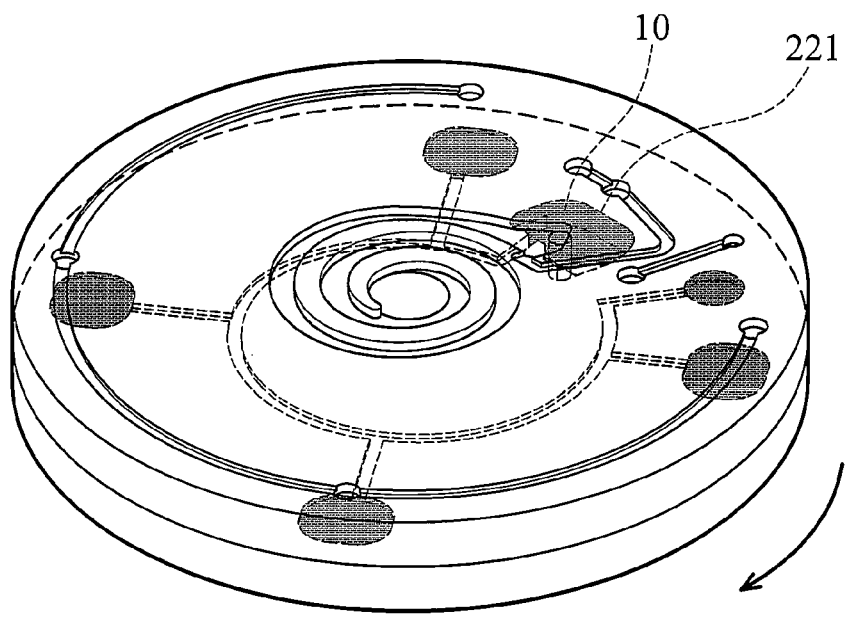
Figure 5C:
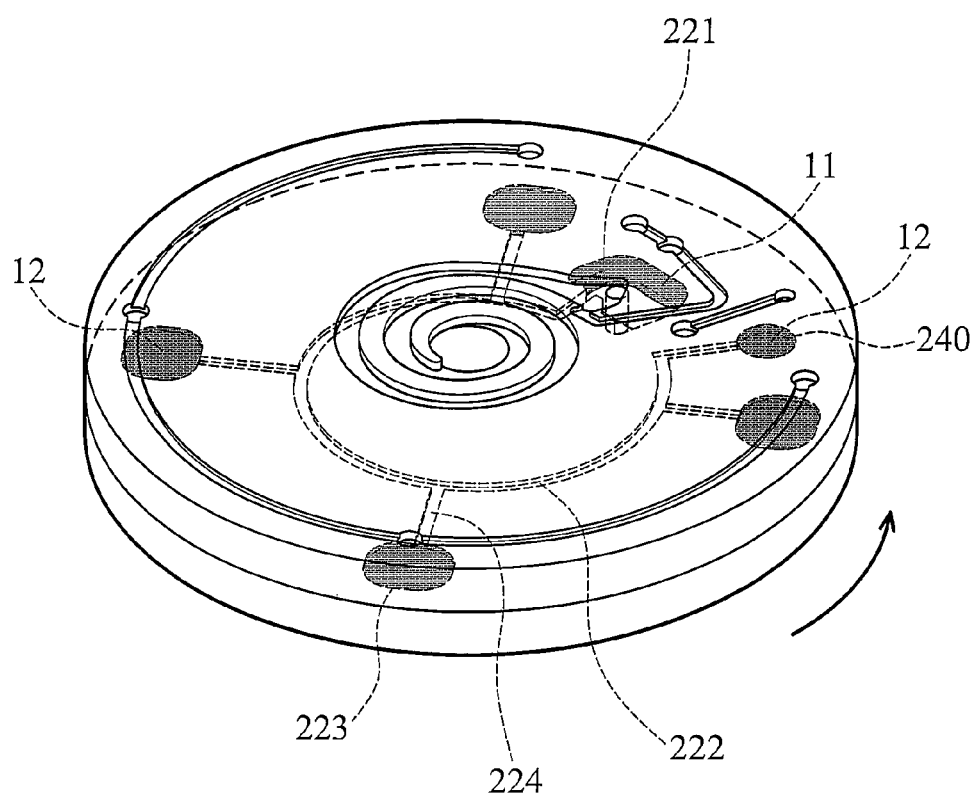

FIGS. 5a-5c show liquid separation process of the fluid analytical device 200. First, with reference to FIG. 5a, fluid (blood) 10 is infused in the spiral groove 211. Then, with reference to FIG. 5b, the fluid analytical device 200 is rotated in a first direction (clockwise) under a first speed, wherein the fluid 10 enters the first separation room 221, and the first fluid constituent (blood cells) 11 is separated from the second fluid constituent (plasma) 12 in the first separation room 221. Finally, with reference to FIG. 5c, the fluid analytical device 200 is rotated in a second direction (counter clockwise) under a second speed, wherein the second fluid constituent (plasma) 12 flows from the first separation room 221, passing the second drain 222 and the capillaries 224, and enters the second separation room 223. Superfluous second fluid constituent (plasma) 12 enters the waste liquid room 240, and the first fluid constituent (blood cells) 11 stays in the first separation room 221.

The first speed is greater than the second speed. When the fluid 10 enters the first separation room 221, the second separation room 222 and the waste liquid room 240, air in the first separation room 221, the second separation room 222 and the waste liquid room 240 is exhausted through the first exhaust groove 231, the second exhaust groove 232 and the third exhaust groove 233.

The fluid analytical device of the invention quickly separates fluid with a simpler structure and lower cost.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:
1. A fluid analytical device, comprising:
a body rotatable around an axis to generate a centrifugal force;
a reservoir, formed on the body;
an inlet channel, formed on the body connected to the reservoir;
a separation recess, formed on the body radially outward from the reservoir and connected to the inlet channel, wherein the separation recess is a single recess comprising:
a pile area;
a collecting area, radially located between the pile area and the reservoir, wherein the pile area is in line with and entirely radially outward from the collection area relative to the axis; and
a spacing wall, formed between the pile area and the collecting area, wherein the spacing wall is a protrusion protruding into the flow path of the liquid such that a top of the spacing wall is higher than a bottom surface of the pile area and collecting area, and wherein the pile area is further from the axis than the collecting area, and the inlet channel connects to the pile area at a location above the spacing wall; and
an exhaust channel connecting the collecting area and the reservoir;
wherein the reservoir, separation recess, and inlet channel are arranged such that the centrifugal force moves a liquid from the reservoir to the pile area via the inlet channel, and a first fluid constituent of the liquid remains in the pile area while a second fluid constituent of the liquid moves over the spacing wall to the collecting area due to a specific weight difference therebetween.
2. The fluid analytical device as claimed in claim 1, wherein a volume of the collecting area is smaller than a volume of the pile area.

3. The fluid analytical device as claimed in claim 1, wherein a volume ratio between the pile area and the collecting area is between 1:1 and 2:1.
4. The fluid analytical device as claimed in claim 1, wherein a ratio between a depth of the spacing wall and a depth of the collecting area is between 1/3 and 1/6.
5. The fluid analytical device as claimed in claim 1, wherein the reservoir comprises a spiral groove formed on a bottom thereof.
6. The fluid analytical device as claimed in claim 1, wherein the spacer further comprises a plurality of guiding grooves formed on a top thereof.
7. The fluid analytical device as claimed in claim 1, wherein the fluid is blood, the first fluid constituent is blood cells, and the second fluid constituent is plasma.
8. A fluid analytical method for separating a first fluid constituent and a second fluid constituent, comprising:
providing the fluid analytical device as claimed in claim 1; and
rotating the fluid analytical device to separate the first and second fluid constituents, wherein the fluid analytical device is rotated with respect to the reservoir.
9. A fluid analytical device, comprising:
a body rotatable around an axis to generate a centrifugal force;
a reservoir, formed on the body;
a plurality of inlet channels, formed on the body connected to the reservoir;
a plurality of separation recesses, formed on the body radially outward from the reservoir and surrounding the reservoir, wherein each of the separation recess is connected to the inlet channel, and comprises:
a pile area;
a collecting area, radially located between the pile area and the reservoir, wherein the pile area is in line with and entirely radially outward from the collection area relative to the axis; and
a spacing wall, formed between the pile area and the collecting area, wherein the spacing wall is a protrusion protruding into the flow path of the liquid such that a top of the spacing wall is higher than a bottom surface of the pile area and collecting area, and wherein the pile area is further from the axis than the collecting area, and the inlet channel connects to the pile area at a location above the spacing wall; and
a plurality of exhaust channels respectively connecting the collecting area of each separation recess and the reservoir;
wherein the reservoir, separation recesses, and inlet channels are arranged such that the centrifugal force moves a liquid from the reservoir to the pile areas via the inlet channels, and a first fluid constituent of the liquid remains in the pile areas while a second fluid constituent of the liquid moves over the spacing walls to the collecting areas due to a specific weight difference therebetween.
10. The fluid analytical device as claimed in claim 9, wherein the separation recesses are arranged equidistantly.
11. A fluid analytical method for separating a first fluid constituent and a second fluid constituent, comprising:
providing the fluid analytical device as claimed in claim 9; and
rotating the fluid analytical device to separate the first and second fluid constituents, wherein the fluid analytical device is rotated with respect to the reservoir.

* * * * *